(12) United States Patent
Reuss

(10) Patent No.: US 6,449,501 B1
(45) Date of Patent: Sep. 10, 2002

(54) PULSE OXIMETER WITH SIGNAL SONIFICATION

(75) Inventor: James L. Reuss, Waukesha, WI (US)

(73) Assignee: OB Scientific, Inc., Germantown, WI (US)

( * ) Notice: Subject to any disclaimer, the term of this patent is extended or adjusted under 35 U.S.C. 154(b) by 0 days.

(21) Appl. No.: 09/579,648

(22) Filed: May 26, 2000

(51) Int. Cl.[7] .................................................. A61B 5/00
(52) U.S. Cl. ........................ 600/323; 600/330; 600/336; 600/322
(58) Field of Search ........................ 600/309–311, 313, 600/315–316, 322–328, 336–342, 330, 338; 356/39–41

(56) References Cited

U.S. PATENT DOCUMENTS

| | | | | |
|---|---|---|---|---|
| 4,869,253 A | * | 9/1989 | Craig, Jr. et al. | 600/323 |
| RE33,643 E | * | 7/1991 | Isaacson et al. | 600/336 |
| 5,218,962 A | * | 6/1993 | Mannheimer et al. | 600/331 |
| 5,627,531 A | * | 5/1997 | Posso et al. | 341/22 |
| 5,830,135 A | * | 11/1998 | Bosque et al. | 600/323 |
| 5,912,656 A | * | 6/1999 | Tham et al. | 345/418 |
| 6,035,223 A | | 3/2000 | Baker, Jr. | |
| 6,083,172 A | * | 7/2000 | Baker, Jr. et al. | 600/500 |
| 6,175,752 B1 | * | 1/2001 | Say et al. | 600/345 |

FOREIGN PATENT DOCUMENTS

EP 0261787 A 3/1988

* cited by examiner

*Primary Examiner*—Eric F. Winakur
*Assistant Examiner*—Matthew Kremer
(74) *Attorney, Agent, or Firm*—Reinhart Boerner Van Deuren, S.C.

(57) ABSTRACT

An improved pulse oximeter is disclosed. The pulse oximeter includes audio signal generation means, controlled by algorithms in a processing element which continuously transform the signals from the sensor into signal quality information. This information is converted into an audio signal and annunciated for the operator's use in guiding sensor placement. This signal quality information is available even in the absence of successful computation of pulse rate and/or oxygen saturation level. It furthermore can reflect signal quality changes that may be too subtle to be reflected in the typical numerical representation of pulse rate and oxygen saturation trend. The audio representation of the signal quality can further be modulated to convey other system and/or physiological status and alerts.

29 Claims, 7 Drawing Sheets

PULSE OXIMETER WITH SIGNAL SONIFICATION

FIELD OF THE INVENTION

The present invention relates generally to pulse oximetry devices and methods. More particularly, the invention is concerned with a pulse oximetry system that provides enhanced signal quality information to the operator via signal sonification, in order to improve monitoring accuracy and availability.

BACKGROUND

Pulse oximeters are well known in the art. Typically, such devices comprise a sensor with light emitting device(s) and associated photodetector(s), attached to a monitoring device performing signal acquisition, analysis, and display/print functions. One particular example of a pulse oximeter is described in U.S. Pat. No. 5,842,981.

The signals acquired from a pulse oximeter are proportional to the tranmissivity of the biological tissues at the sensor. When visualized as photoplethysmographic waveforms, pulsations are visible occurring in synchrony with the heart rate. These pulsations result from the increased absorption of light occurring during passage of blood through the arterial system. Because the arterial pulsation is the result of systole in the heart, this rapid increase in absorption (decrease in detected light intensity) is referred to herein as the systolic phase of the signal. The intervening time between systolic phases, characterized by a relatively gradual decrease in absorption, is herein referred to as the diastolic phase. By choosing appropriate wavelengths of light, the plurality of oximetry signals can be interpreted to yield the percentage of saturation of the hemoglobin molecules with oxygen ($SpO_2$). In the prior art, red and infrared pulsatile amplitudes, scaled by their respective mean light intensities, are combined in a ratiometric equation to yield a ratio related to $SpO_2$.

The pulsatility of the photoplethysmographic waveform is very distinctive, resembling an inverted arterial blood pressure waveform even to the extent that a dichotic notch is often visible. (This similarity is commonly emphasized by inverting the photoplethysmographic waveform.) Like the arterial pressure waveform, the oximetry signals represent the hemodynamic activity of the cardiovascular system, rather than electrical activity of the heart like an ECG. Hence oximeters often provide a means of signal visualization to convey signal quality as well as physiological information (such as the pulse rate and rhythmicity).

Successful physiological monitoring, including pulse oximetry, depends upon acquisition of usable signals from the sensor(s). One problem associated with pulse oximetry is that signal quality can be highly dependent upon sensor placement and the condition of the underlying tissue. This problem is relatively worse in reflectance mode pulse oximetry, wherein signals are typically of lower intensity.

Reflectance pulse oximetry appears, however, to be the only viable method for in utero fetal pulse oximetry. The sensor is inserted into the uterus of a mother to noninvasively monitor the condition of a fetus, a mother, and a placenta. One particular example of a sensor designed for fetal pulse oximetry is described in U.S. Pat. No. 5,425,362. The sensor placement is made through the birth canal to reach a monitoring position on the fetus. This process and its outcome are difficult to satisfactorily visualize, even utilizing intrauterine imaging technologies such as ultrasound. Thus, fetal pulse oximetry represents a challenging scenario for signal acquisition in medical monitoring.

Clinical experience with fetal pulse oximetry bears this out. A recent study looking at 164 cases in which fetal oxygen saturation could be measured found that reliable signals were available only 64.7% of the time during the first stage of labor, and even less during the second stage of labor (Goffmet et al, 1997). Other studies have reported still lower availability. This percentage of monitoring availability is much less than experienced in clinical practice when using pulse oximetry in adults or even neonates, indicating the difficulty of fetal oxygen saturation monitoring and the need for further improvement.

Thus, it is important to provide the clinician assistance in assessing the efficacy of sensor placement by indirect means, but commercially available systems have failed to satisfy this requirement. The prior art suggests several possible solutions.

In one prior art fetal oximetry sensor, described in U.S. Pat. No. 5,247,932, electrical impedance is monitored near the sensor's active components to detect whether the sensor is in contact with tissue. If both electrodes are bathed in amniotic fluid, the impedance is lower than when one electrode is in contact with wet tissue. A high impedance interface, however, does not guarantee that the tissue site is suitable for pulse oximetry, i.e., adequately perfused and free of interfering material. Nor does impedance measurement alone tell whether the signal quality will be better or worse than that of another site with similar interface impedance, or even if the site is on the fetus and not the mother.

Audio pulse tone generation has been employed in prior art pulse oximeters, an early example of which was described in U.S. Pat. No. 4,653,498. The prior art devices generate a simple tone for each identified pulse. In a further enhancement revealed in the patent, the tone pitch is proportional to the oxygen saturation level. Although useful for providing pulse rate and oxygen saturation trend information, this technique is inadequate for signal quality representation.

Sonification is the field of study dealing with the expression of information as humanly perceptible sound patterns. The human auditory system is highly sophisticated, featuring impressive dynamic range and parallel processing of many narrow sub-bands of the audible frequency range. This makes the audio medium ideal for expressing information that may contain subtle, time-varying features. Sonification has been suggested as a means of conveying more physiological information to the operator of a medical device, as described in U.S. Pat. No. 5,730,140. That patent teaches that the prior art in pulse tone generation (as cited above) suffers from the limitation of "quantization". That is, the complex, continuous signals acquired from the sensor have been reduced to artificial, simplistic beeps, with a drastic loss of information. The present invention seeks to avoid the information loss inherent in quantization.

The type of quantized pulse tone generation revealed in the prior art is dependent upon successful completion of a chain of algorithmic operations directed at accurately identifying pulsatile events in the input signals. With variations in design and implementation, analogous steps are performed in all pulse oximeters. The purpose of this signal filtering, pulse detection, and ratiometric computation is to obtain the pulse rate and oxygen saturation values, updating them on a relatively frequent basis (ideally, every pulse). These algorithms are generally tuned to rigorously avoid false positive pulse identification, as might occur during conditions of poor signal quality, since false pulses could result in erroneous pulse rate and/or oxygen saturation readings. Therefore, any condition compromising signal quality is likely to result in silence or merely a sporadic audio signal, without helping to discriminate the reason for the signal quality problem (movement, poor perfusion, low illumination level, etc.).

There remains a need for a pulse oximeter providing continuous signal quality information to the operator with rapid response to changing conditions at the sensor-tissue interface and little time delay. Such signal quality information would preferably be conveyed to the operator without requiring full attention to a visual display. That is, the operator should be capable of perceiving the signal quality information even while concurrently attending to the patient or manipulating the sensor. Preferably, the signal quality information would guide the operator during sensor adjustments intended to improve signal quality, that is, convey a spectrum of quality information rather than a quantized quality metric. The signal quality information would provide early warning of deteriorating signal quality before complete loss of pulse rate or oxygen saturation tracking. Lastly, the signal quality information should be made available in such a way that other information, for example, the physiological status of the patient and physiological or system alerts, can also be conveyed in parallel. The present invention meets these requirements by creating an audio signal based on sonification of the sensed signals.

It is therefore an object of the invention to provide a pulse oximeter with enhanced signal quality information to the operator.

It is another object of the invention to provide a pulse oximeter system in which signal quality may be represented continuously via sonification of the signals.

It is still another object of the invention to provide a pulse oximeter system in which further physiological information, such as oxygen saturation level, can be modulated into the same audio signal.

It is yet another object of the invention to provide a pulse oximeter system in which physiological or system alerts can be modulated into the same audio signal.

SUMMARY OF THE INVENTION

In the present invention, pulse oximetry is made more effective by continuously transforming the input signals from the sensor into an audio signal, augmenting or replacing visual representations of signal quality. This audio signal is available for the clinician's use in guiding sensor placement even in the absence of successful computation of pulse rate and/or oxygen saturation level. Furthermore, various features of the audio signal are used to distinguish how good sensor placement may be, i.e., how robust the pulse detection will be if the sensing is perturbed by interfering factors such as pressure, slippage, etc.

The input signals from the sensor are typically indicative of the amount of light not absorbed by the blood-carrying tissue it has been transmitted though by at least two light emitting devices. Preferably, a number of steps are taken to condition the input signal and to accentuate the pulsatile components of the input signal before transforming the input signal to an audio signal.

Preferably, the input signals are initially conditioned to remove noise, due to ambient light, fluctuations on the input power line, drift, and high frequency interference. Other filters, for removing noise due to motion artifacts, or other sources, are also possible.

Once clean input signals are obtained, the filtered input signals can be further processed to accentuate the pulsatile components. For example, in one embodiment of the present invention, each of the input signals is differentiated with respect to time. The two signals are then merged and passed through a limiter which limits the amplitude of each pulse between pre-established "floor" and "ceiling" parameters indicative of a good quality signal. A "clipped" signal which is clipped off at both the floor and ceiling is indicative of high quality input data, while a signal that is not clipped is less reliable. Prior to transforming the signal to audio, the input signal can also be evaluated to determine "peak" and "valley" levels at each pulse in the signal. These values can be used to dynamically modify the volume of the output audio such that a low volume signal indicates a lower quality signal as compared to a higher volume output. Furthermore, higher volume peaks and lower (or zero) volume valleys can be used to indicate systole and diastole phases of the heartbeat, respectively.

The resultant audio signal can be combined or merged with other audio alerts in the oximetry system. For example, in the event of a predetermined physiological alert condition or a system problem, the audio component of the oximeter can be constructed to provide an alert tone. Depending on the severity of the alert, the audio signal indicative of signal quality can be suppressed. Alternatively, the alert signal can be added to the audio signal.

Preferably, the signal transformation phase accentuates the pulsatile nature of the signals by a combination of filtering and differentiation in the time domain. As previously noted, the pulsatility of the photoplethysmographic waveform is quite distinctive and informative to the trained operator. Furthermore, interfering factors generally disturb this natural pulsatility, making it a natural feature to employ in assessing signal quality.

In another preferred embodiment of the invention, modulating the audio volume differently during systolic and diastolic phases of the signal further emphasizes the pulsatile nature of the input signals. In yet another preferred embodiment, one or more physiological parameters are encoded in the audio signal. In a highly preferred embodiment, the oxygen saturation is represented in the audio signal by adjusting the continuous tone frequency such that the peak frequency of the systolic phase of a particular pulsation represented in the audio signal is proportional to the recent oxygen saturation trend level.

In one highly preferred embodiment of the invention, the pulse oximeter system comprises a fetal sensor for monitoring oxygen saturation in the blood of a fetus while in the womb.

Other advantages and features of the invention, together with the organization and manner of operation thereof, will become apparent from the following detailed description when taken in conjunction with the accompanying drawings wherein like elements have like numerals throughout the drawings.

DETAILED DESCRIPTION OF THE PREFERRED EMBODIMENT

Figure 1:
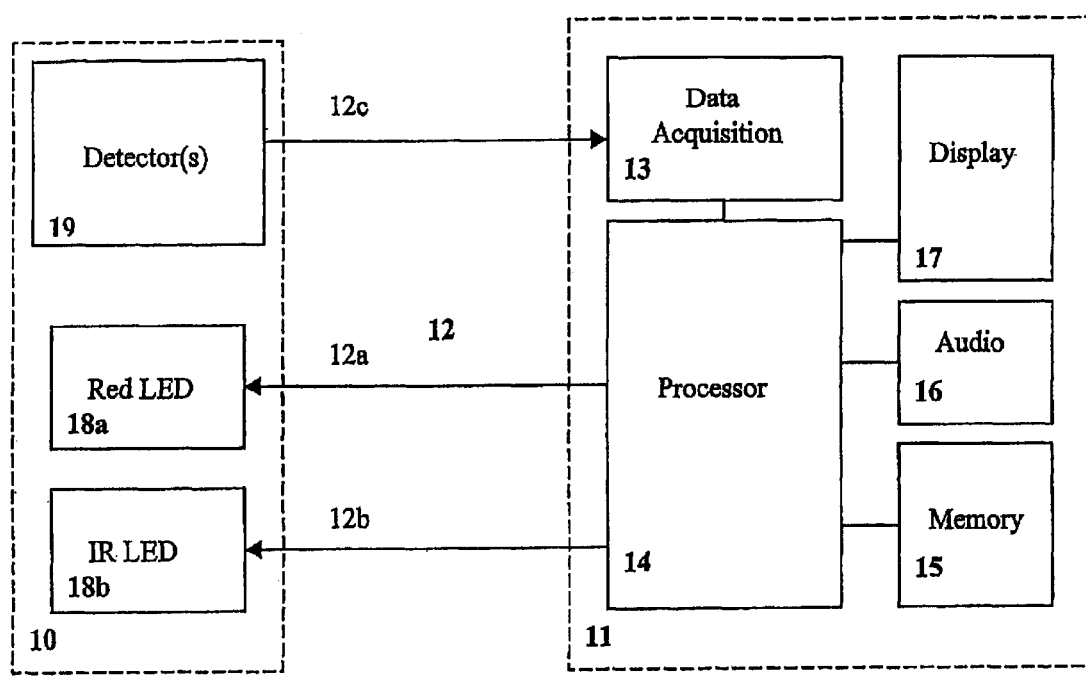
FIG. 1 is a block diagram of a pulse oximetry system constructed in accordance with one embodiment of the present invention.
Figure 2:
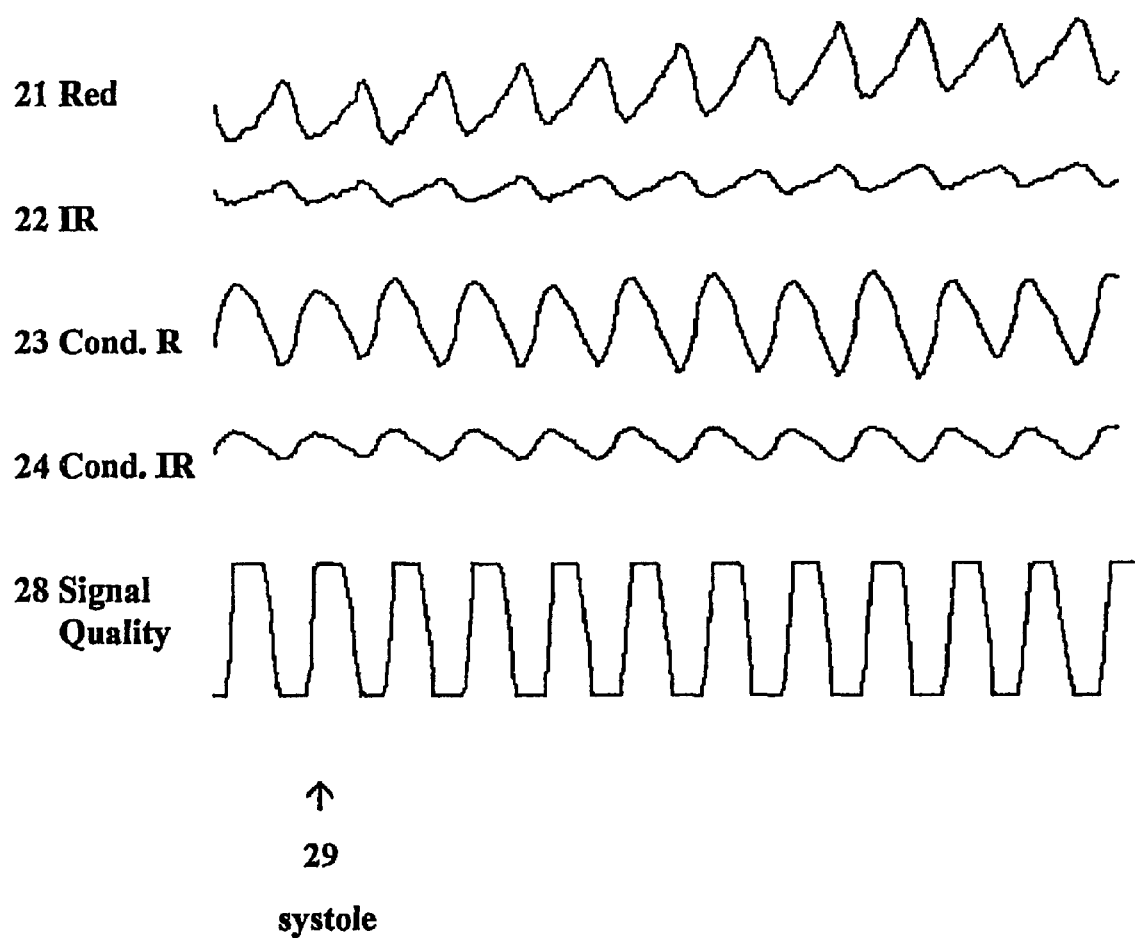
FIG. 2 is a representative sample of various signals obtained from an enhanced pulse oximeter in accordance with one embodiment of the invention, under high signal quality conditions.

A typical pulse oximeter is illustrated in FIG. 1. A representation of the input signal and the resultant signal at various stages as the signal is processed prior to the transformation of the input signal to an audio representation in accordance with the present invention is shown in FIG. 2. To obtain the input signals 21 and 22, a sensor 10 comprising light emitting devices 18a and 18b and a detector 19 is initially coupled to blood-carrying tissue. In some applications, the light emitting devices 18a and 18b will be directed at the tissue, and the detector 19 positioned on the opposite side of the tissue to determine the amount of absorbed light. Such a connection, for example, can be made through a finger or an ear lobe. In the case of fetal oximetry, as noted above, the sensor 10 is inserted into the uterus of a mother to noninvasively monitor the condition of a fetus. Rather than detecting light transmitted through the tissue site, in a reflectance sensor the detector 19 receives the portion of the light from the light emitting devices 18a and 18b which has scattered back to the surface from the tissue beneath the sensor. Fetal monitoring, therefore, poses a number of significant problems. For example, medical personnel cannot visually determine whether the sensor has been adequately coupled to the tissue of the fetus. Furthermore, noise is significantly higher in reflectance-based oximetry than in absorption-based oximetry.

The red input signal 21 and infrared input signal 22 of FIG. 2 are indicative of the light returning from the blood-carrying tissue as detected by the detector 19. These signals are preferably conditioned through analog or digital signal processing in the oximeter 11 to remove noise, as described below, resulting in the conditioned signals 23 and 24. As noted above, since noise is particularly acute in reflectance-based oximetry, noise removal steps are particularly important in fetal oximetery. These steps, however, are also important for monitoring in noisy environments, and are beneficial in all environments.

Figure 3:
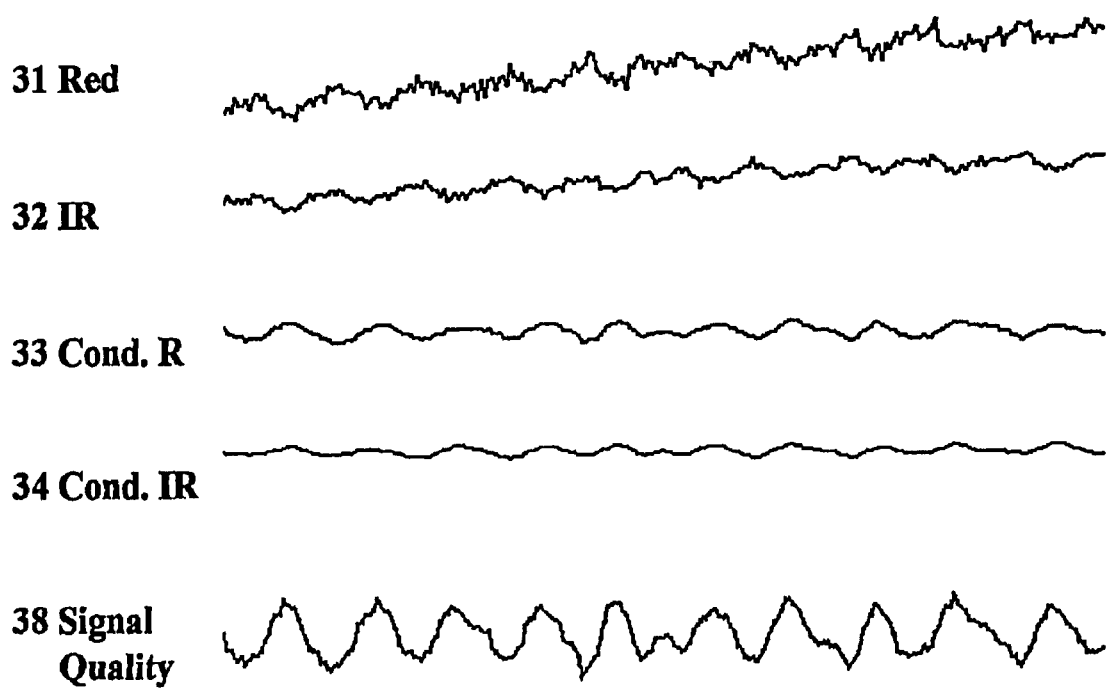
FIG. 3 is a representative sample of various signals obtained from an enhanced pulse oximeter in accordance with one embodiment of the invention, under low signal amplitude conditions.

Pulsatile components of the signals 23 and 24 can then be emphasized in order to differentiate between a good quality sensor connection (28, FIG. 2) and a poor or low quality connection (38, FIG. 3). Furthermore, pulsatile components can be examined and filtered to eliminate poor signals prior to determining blood oxygenation or other physiological parameters. These steps will also be described more fully below. Upon completion of the signal processing steps, the resultant signals can be mapped to an audio frequency to provide an aural representation of the quality of the sensor placement, to provide an aural representation of oxygen saturation and other physiological parameters, and to provide other alert signals as described below. Due to the transformation to audio, medical personnel can position the sensor and/or obtain feedback related to monitored physiological parameters without the need for diverting their attention to a display.

Referring again to FIG. 1, a pulse oximeter commonly consists of a sensor (10) for application to a tissue site (either human or animal), connected to a monitor unit (11) by electrical wiring (12). The sensor contains light sources (18), typically light-emitting diodes (LEDs) controlled by the monitor and photodetector(s) (19) returning signal(s) to the monitor. The wiring (12) carries control signals to the sensor (10) and input signals back to the monitor unit (11). Here, the control signals are directed from the processing circuit (14) to the red and infrared LEDs (18) along wire (12a) and (12b) while the signal(s) from the photodetector(s) are directed to the data acquisition circuitry (13) along the wire (12c). The input signals (21 and 22) are derived from the photodetector(s) as determined by the particular configuration of sensor and data acquisition circuitry (see below). The monitor unit (11) contains various components schematically indicated here, including data acquisition circuitry (13), processing capability (14), memory circuitry (15), audio signal output (16), and visual display plus keypad or other operator controls (17). One example of an oximeter constructed in accordance with the block diagram of FIG. 1 is disclosed in U.S. Pat. No. 5,842,981, which is hereby incorporated by reference. Generally, the processing circuitry (14) drives the light sources (18) and processes received signals from the detector (19) to calculate blood oxygenation or other physiological parameters. The data acquisition circuitry (13) digitizes the analog signal for use by the processing circuitry (14), and, in some cases, may provide analog processing of analog signals. In the present invention, it is assumed that the audio signal output component (16) is capable of generating at least one "voice" with a dynamically varying frequency within a relatively wide audible frequency range.

Variations of this design have been revealed, relating to the location number and nature (frequencies) of the light source(s), transfer of the signals between sensor and monitor, intended use of the sensor at different tissue sites, features of the monitor unit including variations in signal processing techniques, packaging of the sensor or monitor components, processing in embedded versus general-purpose computing devices, distribution of components over a network, etc. These variations do not change the fundamental principles and limitations of pulse oximetry.

For example, although a pulse oximeter employing two light emitting devices, oximeters which employ three or more light emitting devices could also be employed in the present invention. Furthermore, although a single photodetector is shown, it will be apparent to one of ordinary skill in the art that various types and numbers of photodectors can be used. The only limitation on the photodetectors is that the photodetectors be capable of detecting light transmitted by all of the light emitting devices in the oximeter.

In particular, the signals acquired from the sensor (10), for example as illustrated in FIG. 2, represent pulsatile phenomena related to the circulatory system activity of the organism whose tissue is being monitored. Furthermore, the strength of these signals is dependent upon the sensor type as well as characteristics of the tissue underlying it (pigmentation, vascularization, etc.) Lastly, the signals are subject to disturbance by changes in the sensor-tissue interface, such as pressure, lateral movement, etc. For comparison, an example of weaker oximetry signals is shown in FIG. 3.

A common implementation of pulse oximetry involves sequential exposure of the tissue site to light of red and infrared wavelengths. The photodetector(s) of the sensor typically sample light transmitted through or reflected from the tissue repetitively in multiplexed fashion at the time of exposure to each frequency band. (The multiplexing frequency is chosen to be rapid enough such that the phase lag between red and infrared signals is relatively small compared to the inherent frequency content (approximately 0–20 Hz) of the signals.) In FIG. 2, the resulting demultiplexed red and infrared input signals derived from a single photodetector output signal are denoted (21) and (22), respectively. The onset of systole is indicated in FIG. 2 by a marker (29). The input signals (21–22), which represent transmissivity of light of a particular frequency band through the tissue site, drop during systole as a result of increased absorption of light by the bolus of blood passing through the site. More and different wavelengths have been suggested, and various multiplexing frequencies and schemes suggested, but once again these variations do not fundamentally change the problem of signal quality addressed in the present invention.

Figure 4:
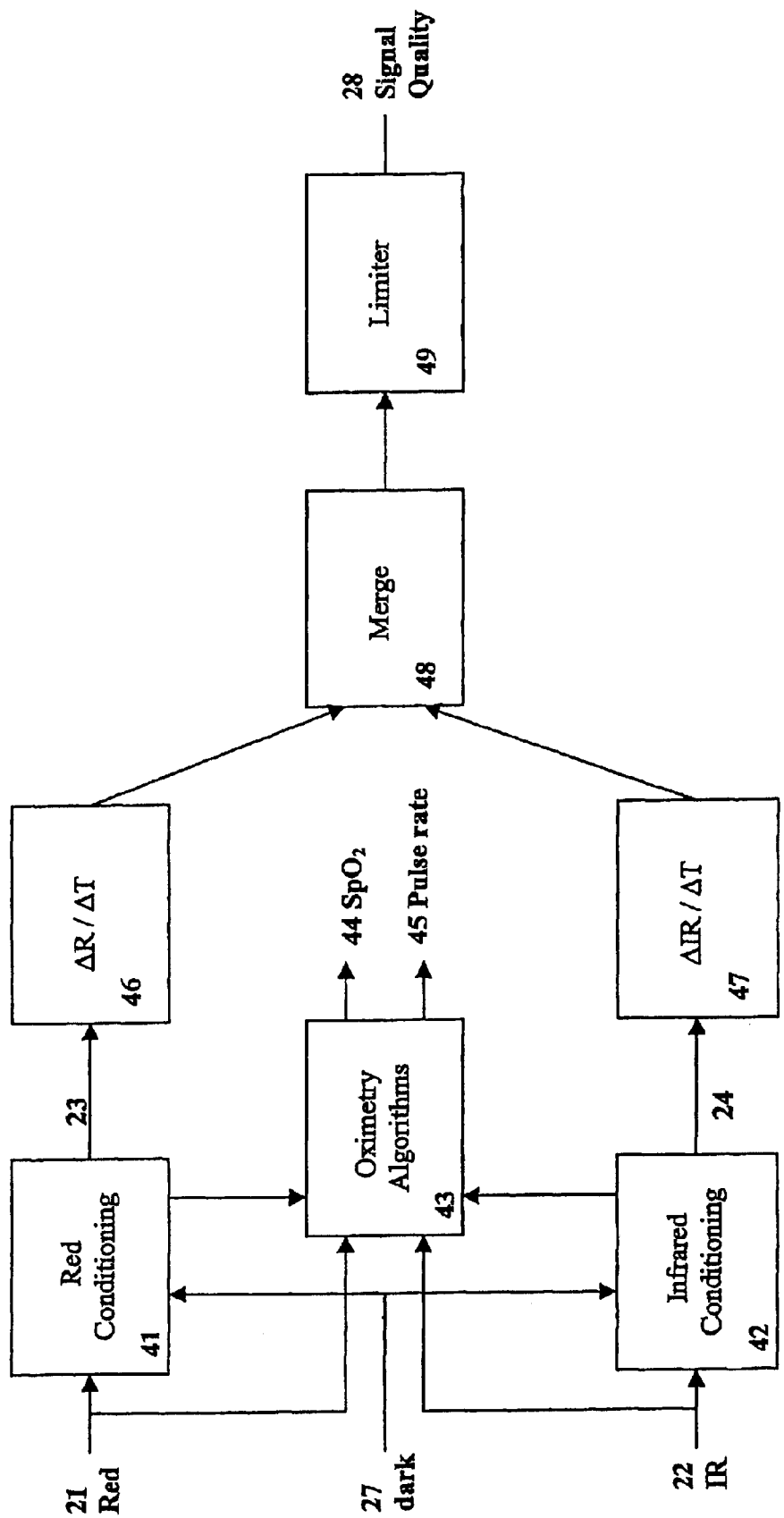
FIG. 4 is a data flow diagram of the signal processing in a pulse oximetry system constructed in accordance with one embodiment of the invention.

The input signals (21 and 22) can undergo signal conditioning, as shown in FIG. 4, to produce the conditioned red (23) and infrared (24) signals illustrated in FIG. 2. This processing, shown as red conditioning (41) and infrared conditioning (42), is intended to remove noise and emphasize signal. Typical signal conditioning can include removal of ambient light bias, line frequency noise rejection, band pass filtering, and signal amplification. Preferably, all of these processes are used to condition the signal. As noted above, conditioning the signal to remove extraneous noise can be particularly important in fetal oximetry, where signals are generally weak and noise is generally significant, particularly due to the use of reflectance-based oximetry. However, it will be apparent to one of ordinary skill in the art that any one signal conditioning process or combination of signal conditioning processes can be used.

If the photodetector(s) of the sensor are exposed to ambient light, the additive noise can add a common-mode bias to the oximetry signals, as well as a range of frequencies depending upon the light source. Removal of ambient light interference occurs, in the preferred embodiment, in the processor (14) after the input signals are converted to the digital domain. However, filtering of the ambient light may also be performed completely or partially in the analog domain, that is, in the data acquisition component (13), without changing the fundamental intention of the step. A "dark" signal (27) is acquired from the sensor (10) by sampling the photodetector(s) in the absence of intentionally applied light from the light emitting device(s) (18a and 18b). The amplitude of this dark signal (27) is tested to detect impinging (and potentially interfering) ambient light. If the level of the ambient light is too high, it may be necessary to disable the oximetry system and alert the operator that the sensor must be repositioned. If the dark signal (27) is at a moderate level, the bias it introduces in the oximetry signals may be eliminated by subtracting the dark signal (27) from each of the input signals (21 and 22). If the subtraction is performed on a sample-by-sample basis, as in the preferred embodiment, then ambient light components in the frequency range of physiological signals may be eliminated from the red and infrared oximetry signals (21 and 22, respectively).

In the preferred embodiment line frequency rejection is performed utilizing a very simple but effective notch filter, The sampling rate is set to twice the fundamental frequency of line noise. Pairs of samples are then added, resulting in reduction of the sampling rate to the line frequency rate. Recalling the trigonometric identity $\sin(\theta)=-\sin(\theta+\pi)$, the result of this operation is counter-phase cancellation of the predominantly sinusoidal line noise with minimal processing. In a given locality, the line power frequency has a nominal rating, typically 50 Hz or 60 Hz; however, in some localities the actual frequency can drift considerably around the nominal value. The sampling rate can be established most effectively by characterizing the line frequency dynamically, for example, with a detector in the line power supply, thereby setting the sampling rate. The resulting samples at line frequency rate can later be resampled to a computationally more convenient rate. It will be apparent to those of ordinary skill in the art that other types of line filters can also be used without departing from the invention.

In the preferred embodiment, the input signals are then band pass filtered to 0.5–10 Hz for removal of drift and high frequency noise. It can be seen in FIG. 2 that, after this conditioning, the polarity of the conditioned signals has been reversed with respect to the red input signal 21 and infrared input signal 22. That is, systole (29) is now marked by a rise in the conditioned signals. This signal conditioning occurs, in the preferred embodiment, in the processor (14) after the input signals (21 and 22) are converted to the digital domain. However, band pass filtering may occur completely or partially in the analog domain, that is, in the data acquisition component (13), without changing the fundamental intention of the step. Further, various alternative implementations for signal conditioning suggested in the prior art, such as adaptive filtering, do not change the fundamental intent of the step. For example, the filter can be reduced to a low pass filter if sufficient dynamic range is available for computations to retain the DC signal components.

In a typical oximetry system, the oximetry signals (the red input signal 21, the infrared input signal 22, and the dark signal 27) and conditioned signals (conditioned red signal 23, and conditioned infrared signal 24) are further processed by oximetry algorithms (43). These algorithms are designed to derive the $SpO_2$ percentage (44) and pulse rate (45) from the signals over a broad range of physiological conditions and possibly in the presence of interfering factors such as motion. The prior art contains many references to alternative implementations for these algorithms. One such algorithm is discussed in U.S. Pat. No. 5,842,981 which is incorporated herein by reference. In the preferred embodiment, pulse detection and qualification is performed to choose pulses suitable for use in the pulse rate and oxygen saturation calculations Because the purpose of the blood oxygenation and pulse rate calculation algorithms is to determine an accurate derivation of trend information these algorithms may not be completely suitable for use in the audio derivation transforms. Therefore signal processing to accomplish these calculations is considered herein as independent of the audio derivation algorithms, or performed at a different stage in the audio derivation algorithms, as shown in FIG. 4.

As a preliminary step in creating an audio signal representing signal quality, it is desirable to emphasize the pulsatile content of the oximetry signals, since the pulsatile content is critical to successful monitoring of physiological parameters and therefore an important indicator of signal quality. As illustrated in FIG. 4, in the preferred embodiment pulsatile content is emphasized through a non-linear combination of the derivatives of the two plethysmographic signals, producing a transformed signal emphasizing variations in the original signals. The conditioned red (23) and infrared (24) signals enter red (46) and infrared (47) differentiators, which produce red and infrared differentiated signals. This step can be performed in the digital or analog domains, depending on the hardware configuration of the pulse oximeter (11). In the digital domain, derivatives are computed on sampled signals by difference equations, that is, $\Delta_i = x_i - x_{i-m}$, where the m-span difference in samples $x_i$ of a signal are taken. In the preferred embodiment, m represents 160 msec, although different spans or combinations of spans are clearly within the scope of the invention. The equivalent in analog circuitry, a signal differentiator, will be familiar to anyone knowledgeable in analog circuit design.

The differentiated signals are combined in a non-linear step (48) causing the differentiated signal with the largest amplitude (i.e., the input signal with the most rapidly rising pulsations) to be emphasized. The merged signal passes through a limiter (49) whose output cannot exceed a selected range determined by a predefined maximum or CEILING and a predetermined minimum or FLOOR. In the preferred embodiment, CEILING and FLOOR are determined empirically to be somewhat narrower than the range of pulsatile variation commonly resulting from strong, high quality input signals. That is, under preferable monitoring conditions, the signal quality data (28) would be expected to clip at a known maximum and minimum, as illustrated in FIG. 2. A clipped signal, therefore, indicates that high quality data is being received from the sensor (10). Referring now to FIG. 3, if the red input signal 31 and infrared input signal 32, are weak, the resultant conditioned signals 33 and 34 also have low amplitude. Under these circumstances, amplitudes are relatively low, and the signal quality data (38) does not reach the CEILING and FLOOR limits, though pulsations are evident. The non-clipped signal quality data (38) of FIG. 3, therefore, indicates that a lower quality signal is received from the sensor (10). The lower quality signal data (38) can indicate that sensor placement is inadequate or is likely to provide less than desirable results. The signal quality data (38) in the preferred embodiment is stored in a circular (ring) buffer, maintained in a fashion well known to anyone familiar with software engineering. Other means of signal storage are possible without changing the intent of the invention.

The processing (differentiation 46 and 47, merge 48, and limiting 49) resulting in the signal quality data (28) tends to enhance the pulsatility in the input signals (21 and 22). Various other mathematical transformations could as easily be employed instead of or in addition to differentiation to emphasize the pulsatility, e.g., a higher-order derivative, higher-power function of the derivative, or a matched filter optimized for the expected shape of the pulsations. These alternatives do not change the fundamental intent of the step.

Figure 5:
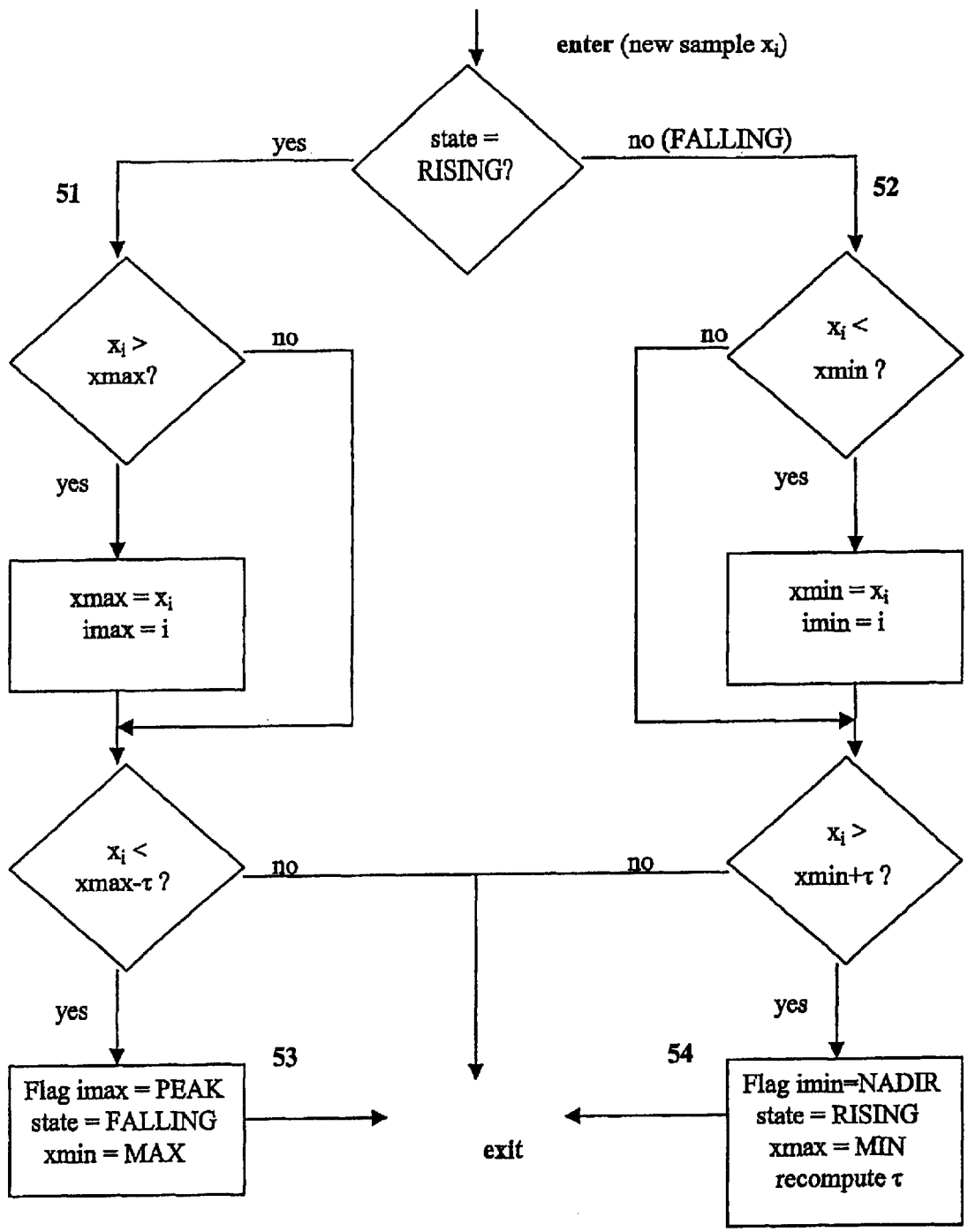
FIG. 5 is a software block diagram of an algorithm for identification of pulsatile phenomena in a signal.
Figure 6:
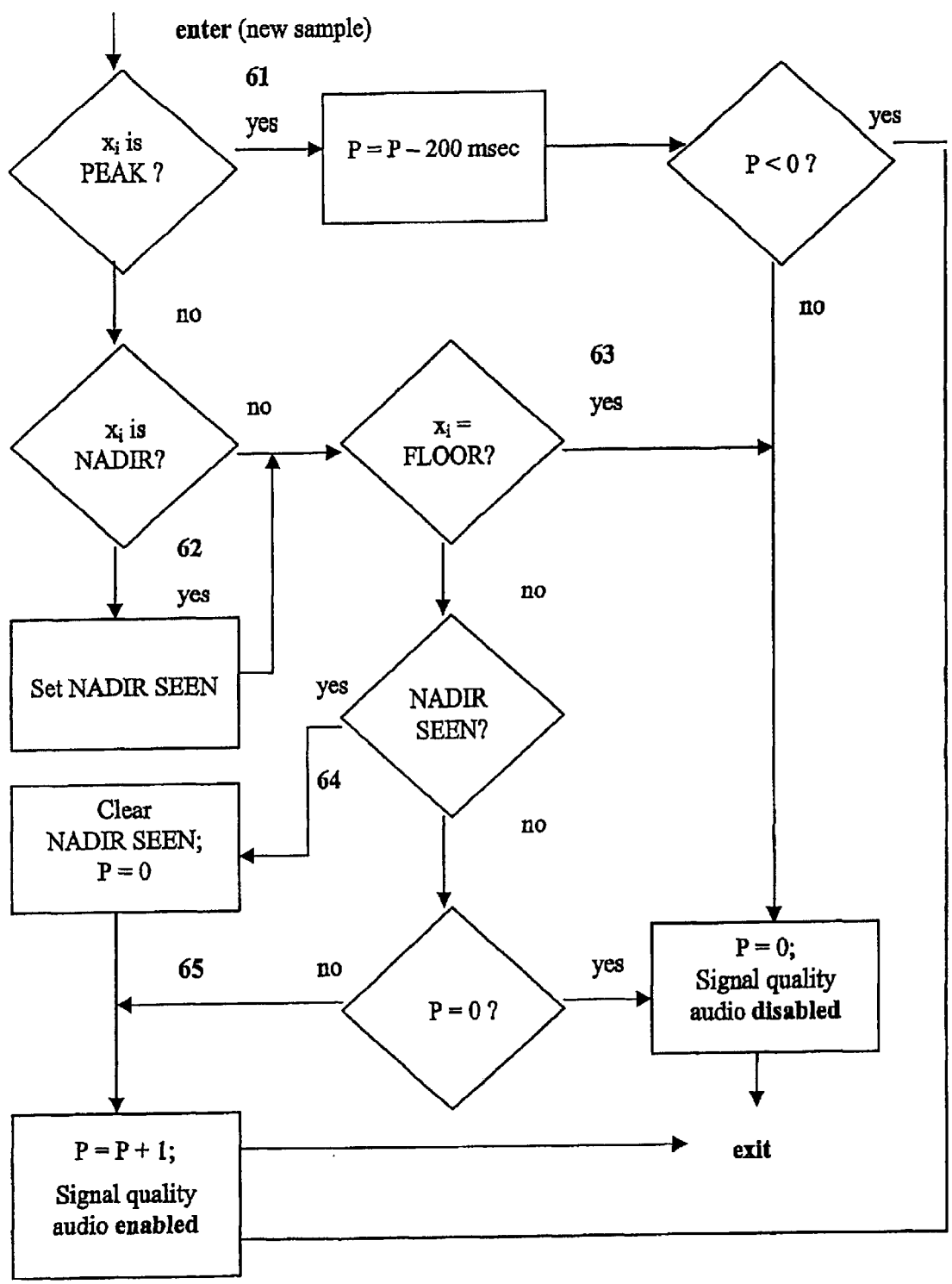
FIG. 6 is a software block diagram of an algorithm for emphasizing pulsatility in an audio signal.

Prior to transforming the signal quality data (28) to audio, an additional processing step designed to accentuate pulsatility can be performed. In the preferred method, an adaptive peak-valley search of the signal quality data (28) is performed to distinguish possible systolic and diastolic phases. This process is illustrated in FIG. 5. The algorithm is controlled by a state variable, with two states, RISING and FALLING. During the RISING branch of the algorithm (51), sampled signal quality data (28) is continually compared to a stored peak signal value. The peak signal value is stored in a variable xmax, and its corresponding time in imax. Similarly, during the FALLING branch of the algorithm (52). the sampled signal quality data (28) is continually compared to a stored minimum value. The nadir of the signal is stored in xmin and its corresponding time in imin. After falling from xmax by at least a predetermined amplitude threshold, $\tau$, the peak is confirmed and a special flag, PEAK, appended to the signal value at imax (53). Similarly, after rising from xmin by at least the predetermined amplitude threshold, the most extreme nadir is confirmed and a special flag, NADIR, appended to the signal value at imin (54). At the nadir, the amplitude threshold $\tau$ is recomputed by $$\tau = \max(\text{NOISE}, k \cdot (xmax - xmin))$$

where k is threshold fraction (greater than zero and less than one) and NOISE is a noise amplitude threshold, below which pulsations are ignored. In the preferred embodiment, k=0.5, although the value may be increased to reduce false identification of pulses or decreased to enhance sensitivity to pulsation. Pulsations below the NOISE level, therefore, are not marked for processing as shown in FIG. 6, although of course they will still be part of the continuous conversion into an audio signal as described below. In either case, the state of the algorithm then flips, and the corresponding extremum is reset (values MAX and MIN) to guarantee update as the alternative branch of the algorithm is entered. The point imax nominally occurs near the end of systole when this algorithm is applied to the signal quality data (28) derived above.

In the further processing of signal quality data (28) that follows, the aforementioned buffered signal quality data (28) is processed with a time delay sufficient to permit the peak identification algorithm to perform, but not long enough to introduce an unacceptable lag between physiologic events and the oximeter's behavior. In the preferred embodiment, the time delay was selected to be 640 msec, although somewhat different time delays can be selected without altering the intent of the invention. Checks are embedded in the pulse identification algorithms to prevent buffer overrun, as will be known to anyone familiar with software engineering. It will be obvious to anyone of ordinary skill in the field that other criteria may be applied to enhance the pulse detection, including template matching, zero crossing analysis, and extraction of other time-domain features such as pulse width. However, it is critical that the processing be such that pulse identification can be accomplished within the specified time delay.

The amplitude of the buffered signal quality data (28) as determined by the imax (53) and imin (54) values is mapped to a frequency range of the audio signal. In - the preferred embodiment, the audio signal is a linear transformation of the signal quality data (28), with the magnitude and offset chosen to produce an audio signal in a desired frequency range. Also, the tone starts low at the end of diastole and rises to a higher frequency during systole, falling again after systole. This range was chosen to be approximately 400 Hz to 1000 Hz in the preferred embodiment. It will be apparent to anyone familiar with the art that the conversion to audio may be accomplished through a linear or more complex function, and that a different frequency range may easily be established. For example, a higher-power function would tend to emphasize the pulsatility of the signal even further.

In the preferred embodiment, the mapping of signal quality to audio frequency, $F_q(\ )$, has the form $$F_q(X) = \max(\text{minf}, \min(\text{maxf}, (\text{floorf} + (x - \text{FLOOR}) \cdot sf)))$$

where $$sf = (\text{ceilingf} - \text{floorf} + 1)/(x\text{ceiling} - \text{FLOOR})$$

Here minf defines the minimum audio frequency and maxf defines the maximum audio frequency such that [minf, maxf] is the full audio frequency range of the audio generating means. Similarly floorf defines the frequency to be associated with the FLOOR or minimum signal quality data (28) level and ceilingf defines the frequency to be associated with the CEILING or maximum signal quality data (28)

level such that, the predetermined frequency scaling (Hz per signal quality units) is represented by sf. The maximum signal quality data value xceiling may be determined in several ways. In the simplest embodiment, xceiling=CEILING, and the highest audio frequency of a pulse is related to the selection of ceilingf plus the pulsatile amplitude or peak as determined above. In this simpler implementation, the lower amplitude pulsations in FIG. 3 would reach a lower maximum audio frequency than those in FIG. 2. In the preferred embodiment, xceiling=xmax, the determined peak for the current pulse (as determined by examining the buffered signal quality data), and the maximum audio output ceilingf frequency is reached on every identified pulsation, regardless of pulse amplitude. Thus pulsations in FIGS. 2 and 3 would all reach the maximum ceilingf frequency.

In the preferred embodiment, the frequency ceilingf corresponding to value xceiling=xmax in the signal quality data (at end of systole in the preferred embodiment) may be adjusted to a desired target frequency. This peak audio frequency may be utilized to encode more information, such as the current oxygen saturation level. Potentially, then, both the peak signal quality data for the peak and the corresponding peak frequency in the audio output could be changing on a pulse to pulse basis. To permit continuous audio signal generation without tonal discontinuities, this frequency adjustment should be made gradually over as much of the systolic phase as possible. This requires calculating sf at every NADIR point in the signal quality data.

The audio signal generated need not be a pure tone. In a preferred embodiment, harmonics of the audio frequency are generated at relatively lower amplitudes. This may have the salubrious effect of decreasing the risk that an operator may be unable to hear the tone due to a partial hearing loss around the tone's frequency. Also, the audio signal may be combined with other audio sources to convey further information (e.g., alarm tones, communications) without changing the intent of the invention.

The audio signal's volume may be controlled dynamically to convey further information about oximetry signal quality, as illustrated in FIG. 6. It is desirable to further emphasize the signal pulsatility by increasing the audio volume during the systolic phase and decreasing it during the diastolic. In the preferred embodiment, the audio volume modulation occurs around an operator-controlled set point. This permits the audio volume to be adjusted for audibility and comfort while still providing dynamic manipulation to convey information. Thus the volume control function $V_q(\ )$ has the form $$V_q(x)=\max\ (minv,\ \min(maxv,\ floorv+(x-FLOOR)\cdot sv))$$

where $$sv=rv/(CEILING-FLOOR)$$

and $$rv=(ceilingv-floorv+1)$$

Here, minv defines the minimum volume and maxv the maximum volume of the audio generating means such that [minv, maxv] in the full volume range of the audio generating means. Similarly, floorv represents a minimum volume and ceilingv a user-controlled maximum volume. Therefore, [floorv, ceilingv] is the audio volume range for signal quality data representation. The number of units in the audio volume range is represented by rv, and sv represents the volume scaling (volume control units per signal quality units). In this way, the audio volume associated with signal quality data at FLOOR will be floorv, and the audio volume associated with CEILING will be the operator-controlled ceilingv, not to exceed maxv. In the preferred embodiment, floorv =minv, so that audio is silent for signal quality data at the FLOOR minimum. Although the amplitude modulation employed in the preferred embodiment is shown as linearly increasing, it may alternatively be non-linear, or the sense of the volume modulation could be reversed, without changing the intent of the invention.

The audio can be silenced completely during diastole, as illustrated in FIG. 6. In FIG. 6, audio control is represented by a variable p. The value of p is maintained such that it is zero only when the audio for signal quality is to be silent. The buffered signal quality data (28), coded with information concerning pulsatile events, is processed sample by sample, wherein each new sample is represented by the variable $x_i$. If a PEAK flag is encountered (61), the current value of p is decremented by a number of samples corresponding to 200 msec. If the result is greater than zero (that is, more than 200 msec have passed since the last nadir), then p is set to zero to silence the audio; otherwise, audio will be allowed to continue (p less than zero) until 200 msec have elapsed. If a NADIR flag is encountered in the data (62), it will be remembered via the NADIR SEEN flag. Lastly, if the signal was clipped at the FLOOR level (63) by the limiter (49), then p is set to zero to silence the audio. If these cases do not apply and the NADIR SEEN flag was set (64), the flag is cleared, the audio control variable p is set to zero, and audio is enabled with pulse width measurement restarted.

After these tests, if the audio control variable p is non-zero (65), it is incremented and the audio representation of the signal quality data is enabled, with the aforementioned $F_q(\ )$ and $V_q(\ )$ mapping the signal quality data to audio frequency and volume, respectively. If the audio control variable p is zero, then the audio is silenced until the next pulsatile event.

This algorithm ensures that silence will occur after a sufficiently pulsatile event in the quality signal data, even though its absolute amplitude may be small. The timing value of 200 msec represents a reasonable maximum amount of time for the rise in absorption associated with systole to take place, and an audio duration easily distinguished by a listener. Although 200 msec has been chosen to produce an adequate tonal representation, it will be apparent that this value could be increased or decreased without changing the intent of the invention.

The amplitude of the signal quality data (28) inherently determines whether the audio silencing during diastole will occur. During low amplitude signal conditions, the audio tone will tend to be continuous, whereas clipping at the FLOOR and CEILING levels will tend to result in silencing during diastole. Thus the pulsations in FIG. 2 would result in discrete tones, whereas those in FIG. 3 will be discrete only if pulsatile amplitude is sufficient. Direct control over this technique permits its selective use when signal quality is judged to be high based on other information. For example, factors such as overall tissue transmissivity (detected light intensity versus strength of light emitted by the sensor) and other quality measures, such as the percentage of pulses found adequate for use in pulse rate and oxygen saturation calculations, may be used to enable the audio silencing technique. In yet another embodiment, the maximum audio volume ceilingv is determined in part by these other indicators of signal quality. In this way, the audio representation of signal quality is loudest (up to an operator-controlled level) when signal quality is determined to be best.

Figure 7:
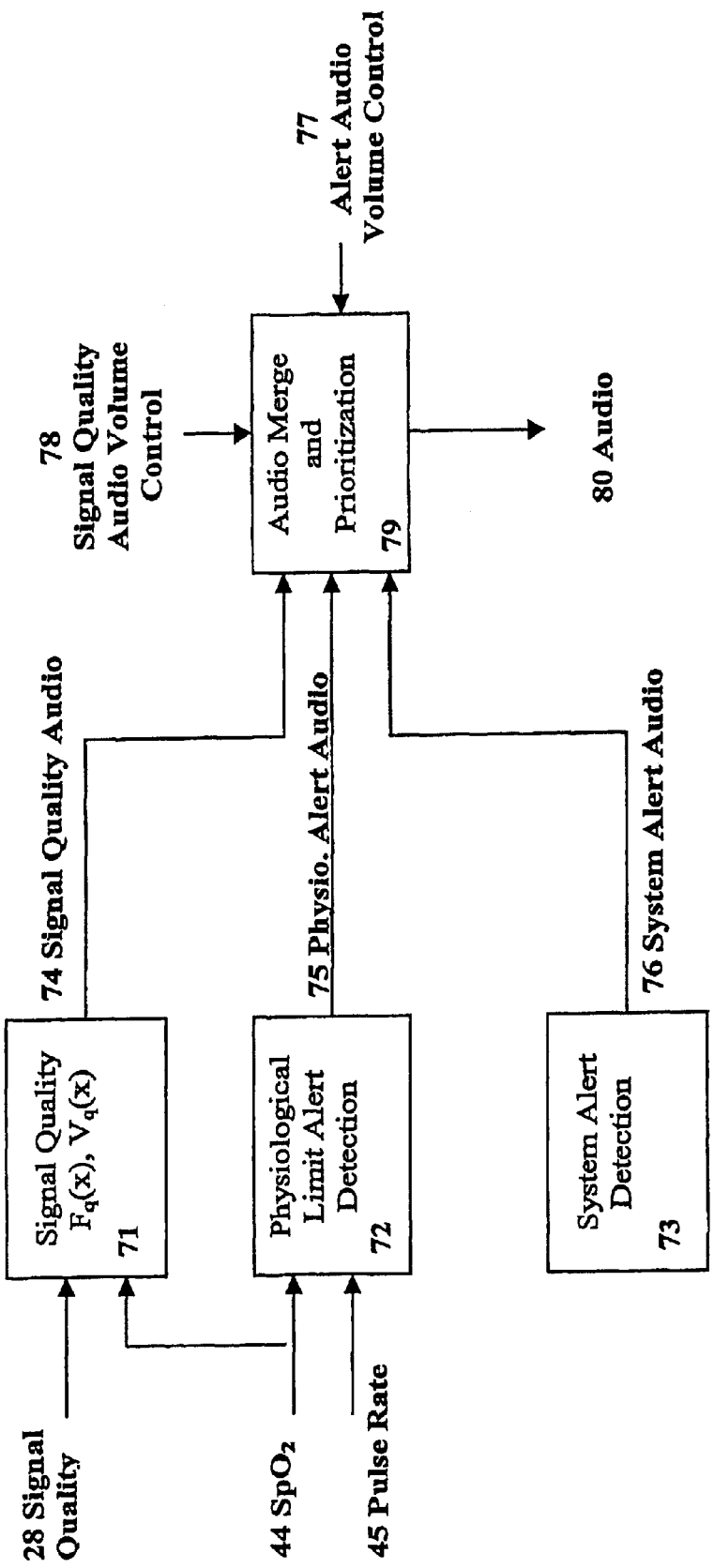
FIG. 7 is a data flow diagram of signal sonification and audio generation in an enhanced pulse oximeter.

Other audio signals, including tones corresponding to physiological and system alerts, can be combined with the audio signal of the preferred embodiment, as illustrated in the overview of FIG. 7. The algorithms of FIGS. 5 and 6 are represented by the Signal Quality step (71), transforming the signal quality data (28) along with $SpO_2$ information (44) into a signal quality audio representation (74). In the preferred embodiment, the signal quality audio representation is merged with other audio sources in the Audio Merge and Prioritization step (79).

The merger of audio sources in the preferred embodiment proceeds as follows. The operator is given independent controls of alert audio volume (77) and signal quality audio volume (78). These controls set overall audio volume of the respective sources, and permits complete suppression of either source. In the preferred embodiment, these controls are performed through the interface software, although they could be implemented as analog controls directly in the audio generating means (16). During periods when the oximetry signals are known to be unusable (for example, if the sensor is disconnected or the light levels produced by the sensor are changing), the signal quality audio (74) is suppressed. The signal quality audio (74) can also be suppressed during physiological alerts (75), which are violations of operator-set limits (72) on the $SpO_2$ level (44) and pulse rate (45) to permit the physiological alert tones (75) to be heard. Under conditions in which poor signal quality data (28) is received from a functioning sensor (10), it is desirable to continue generating signal quality audio (74) and suppress the audio for system alerts (76), which are obviously related to the signal quality, such as a "check oximeter sensor" message (73).

The merged audio signal (80) may be played directly through a speaker or headphones, or conveyed to a remote location in either digital or analog form without changing the intent of the invention. In the preferred embodiment, the audio signal generating means (16) consists of a timer in the processor (14) creating an oscillating digital signal, and an analog control signal. The timer is programmed to create a square wave of 50% duty cycle at the desired audio frequency, and the analog signal level is programmed to the desired audio volume. These two signals are controlled by software in the processor (14) as previously described, and are combined in an amplifier circuit. The end result is an analog voltage (80) for driving a common speaker. Alternative implementations for headphones, playback through a sound system, and so forth should be apparent to anyone familiar with audio technology. Furthermore, although a square wave with 50% duty cycle is described, it will be apparent to those of ordinary skill in the art that other waveforms and other duty cycles could be employed.

Other means are possible for merging multiple audio sources. Multi-voice audio generation can permit the various sounds to occur simultaneously. Alternatively, substantially separate frequency bands may be reserved for alert versus signal quality audio without changing the intent of the invention.

It will be apparent to one familiar with the art that, under optimal conditions of good signal amplitude and low noise, the audio representation of signal quality (74) in the preferred embodiment approaches the stylized beeping of a conventional monitor, including (if desired) conveyance of oxygen saturation level by means of the peak audio frequency reached in each pulsation. This is desirable in that it would be familiar and easily understandable to operators of prior art devices. Under conditions of low signal amplitude, the audio will tend to be continuous, with frequency and volume variations corresponding to the pulsations. The rate and regularity of these variations convey to an operator the adequacy of the signals for monitoring purposes. In terms of optimizing signal quality by utilizing the audio representation, the operator can take as a goal adjusting the sensor (10) of the improved pulse oximeter to achieve a sound quality like a conventional pulse oximetry system operating under optimal conditions.

It should be understood that the transformation to audio can take alternate forms without changing the intent of the invention. For example, the least mean square (LMS) method may be applied to the input (21–22) and/or conditioned (23–24) signals to continuously derive a ratio that can be represented in audio form. This ratio, at pulsatile peaks, is proportional to the oxygen saturation level. Hence, by frequency-encoding the LMS-determined ratio, the peak frequency of the audio signal during pulsatile events would be inherently proportional to the oxygen saturation trend. Furthermore, as noted above, the various filtering and pulsatile accentuation steps listed above are representative only, and it will be apparent to one of ordinary skill in the art that any number of different filtering and accentuation steps and algorithms could be selected based on different monitoring and environmental situations. Furthermore, changes could be made in the processing steps and in the oximeter hardware without departing from the intent of the invention.

While preferred embodiments have been illustrated and described, it should be understood that changes and modifications can be made thereto without departing from the invention in its broadest aspects. Various features of the invention are defined in the following claims.

I claim:

1. A method of enhancing signal quality information using signal sonification while monitoring oxygen saturation in a pulse oximeter comprising the following steps:

(a) exposing a tissue site to a plurality of wavelengths of light generated by the pulse oximeter, said tissue site having one or more pulsatile characteristic(s) associated with physiological parameters;

(b) detecting light of the plurality of wavelengths transmitted by or reflected from components of the tissue site, said detected light having a detected light pulsatile component related to one or more of the pulsatile characteristic(s) of said tissue site, and converting said detected light into a plurality of electrical signals, each said electrical signal of said plurality of said electrical signalshaving an electrical signal pulsatile component related to the detected light pulsatile component;

(c) digitizing and conditioning said plurality of electrical signals in a signal data acquisition component of the pulse oximeter to remove noise while retaining said electrical signal pulsatile component of each of the digitized and conditioned said plurality of electrical signals and creating a plurality of digital signals;

(d) deriving signal quality information from said plurality of digital signals by processing said plurality of digital signals to enhance and accentuate said electrical signal pulsatile component, creating a plurality of enhanced signals; and combining said plurality of enhanced signals to emphasize variations related to said pulsatile tissue characteristic(s) in said plurality of electrical signals from step (b);

(e) continuously transforming said signal quality information into a signal quality audio representation by applying a frequency mapping function and a volume control function;

(f) conveying said signal quality audio representation of signal quality information to an operator;

(g) analyzing said plurality of digital signals for pulse rate and oxygen saturation level;

(h) providing pulse rate and oxygen saturation information to an operator in audible and/or readable form;

(i) combining physiological and system alert information with said signal quality audio representation conveying signal quality information to form a combined audio signal;

(j) permitting operator control of the overall audio volume of said combined audio signal.

2. The method as defined in claim 1, wherein the digitizing and conditioning step includes line frequency rejection and band pass filtering.

3. The method as defined in claim 2, wherein the line frequency rejection in each electrical signal is accomplished by summing of pairs of samples taken at twice the line frequency.

4. The method as defined in claim 2, wherein the band pass filtering passes signal frequencies in the range 0.5–10 Hz.

5. The method as defined in claim 1, wherein the step of deriving signal quality includes differentiation of the digital signals.

6. The method as defined in claim 1, wherein the step of deriving signal quality includes combining the plurality of digital signals to select the one most rapidly varying, and locating pulsatile events in the data.

7. The method as defined in claim 1, wherein the step of transforming signal quality into audio includes mapping signal quality amplitude to a frequency range audible to humans.

8. The method as defined in claim 1, wherein the step of transforming signal quality into audio includes manipulating audio volume to emphasize pulsatility in the plurality of digital signals.

9. The method as defined in claim 8, wherein the manipulation of audio volume includes making audio volume proportional to signal quality data.

10. The method as defined in claim 8, wherein the manipulation of audio volume includes silencing the audio during substantially all of the diastolic phase of pulsations in the plurality of digital signals.

11. The method as defined in claim 1, wherein the step of transforming signal quality into audio includes manipulating the audio volume as determined by a controlling physiological or system parameter.

12. The method as defined in claim 11, in which the controlling parameter is derived from the intensity with which the light emitting devices of the sensor are driven.

13. The method as defined in claim 11, in which the maximum audio volume during a pulsation is proportional to the controlling parameter.

14. The method as defined in claim 1, wherein the step of transforming signal quality into an audio signal includes manipulating the frequency range as determined by a controlling physiological or system parameter.

15. The method as defined in claim 14, in which the controlling parameter is the oxygen saturation trend.

16. The method as defined in claim 14, in which the highest audio frequency of the signal quality audio representation in a particular pulsation is a value proportional to the controlling parameter.

17. The method as defined in claim 1, further comprising the step of combining the audio representation of signal quality with the audio representation of physiological and system alert information.

18. The method as defined in claim 1, where the tissue site is located on an adult or neonatal subject.

19. The method as defined in claim 1, where the tissue site is located on a fetus in utero.

20. A pulse oximeter system with enhanced signal quality information using signal sonification comprising:

a sensor device;

a monitor device comprising at least a data acquisition component, a computing component, a memory storage component, an audio signal generation component, a visual presentation component;

wherein the system is used by (a) exposing a tissue site to a plurality of wavelengths of light generated by the sensor device of the pulse oximeter, the tissue site having one or more pulsatile characteristic(s) associated with physiological parameters;

(b) detecting light of the plurality of wavelengths transmitted by or reflected from components of the tissue site using the sensor device of the pulse oximeter, the detected light having a detected light pulsatile component related to the one or more pulsatile characteristic(s) of the tissue site and converting the detected light into a plurality of electrical signals in the data acquisition component, each of the electrical signals of the plurality of electrical signals having an electrical signal pulsatile component related to the detected light pulsatile component;

(c) digitizing and conditioning the plurality of electrical signals in a signal data acquisition component of the computing component of the pulse oximeter to remove noise while retaining the electrical signal pulsatile component of each of the digitized and conditioned plurality of the electrical signals and creating a plurality of digital signals;

(d) deriving signal quality information from the plurality of the digital signals in the computing component, by processing the plurality of digital signals to enhance and accentuate the electrical signal pulsatile component, creating a plurality of enhanced signals, and combining the plurality of enhanced signals to emphasize variations related to the pulsatile tissue characteristic(s) in the plurality of electrical signals from step (b);

(e) continuously transforming the signal quality information into a signal quality audio representation, by applying a frequency mapping function and a volume control function;

(f) conveying the signal quality audio representation of signal quality information to an operator using the audio signal generation component;

(g) analyzing the plurality of digital signals for pulse rate and oxygen saturation level;

(h) providing pulse rate and oxygen saturation information to an operator in audible form using the audio signal generation component and/or readable form using the visual presentation component;

(i) combining physiological and system alert information with the signal quality audio representation conveying signal quality information to form a combined audio signal;

(j) permitting operator control of the overall audio volume of the combined audio signal using the audio signal generation component.

21. The pulse oximeter as defined in claim 20, wherein the sensor device comprises a plurality of light emitting devices and at least one associated detector, the light emitting devices and the at least one associated detector being used for measuring oxygen saturation.

22. The pulse oximeter as defined in claim 20, wherein the computing component is used to derive signal quality information from the sensor device.

23. The pulse oximeter as defined in claim 20, wherein the audio signal generation component is used to convey the signal quality information to an operator.

24. The pulse oximeter as defined in claim 20, wherein the audio signal generation component includes a headset.

25. The pulse oximeter as defined in claim 20, wherein the audio signal generation component includes a speaker.

26. The pulse oximeter as defined in claim 20, wherein the audio signal generation component includes a connection for an external sound system.

27. The pulse oximeter as defined in claim 20, wherein the audio signal generation component includes a connection for a remote annunciator.

28. The pulse oximeter as defined in claim 20, wherein the sensor device is designed for use in monitoring adults or neonates.

29. The pulse oximeter as defined in claim 20, wherein the sensor device is designed for use in fetal monitoring.

* * * * *